(12) United States Patent
Helmy et al.

(10) Patent No.: US 10,420,640 B2
(45) Date of Patent: Sep. 24, 2019

(54) DETECTING COATINGS ON INTRAOCULAR LENS INSERTION DEVICES AND METHODS OF MANUFACTURING THE DEVICES

(71) Applicant: Johnson & Johnson Surgical Vision, Inc., Santa Ana, CA (US)

(72) Inventors: Ahmed Helmy, Palm Desert, CA (US); Peiwen Cheng, Aliso Viejo, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 185 days.

(21) Appl. No.: 15/413,253

(22) Filed: Jan. 23, 2017

(65) Prior Publication Data

US 2017/0128195 A1  May 11, 2017

Related U.S. Application Data

(62) Division of application No. 13/717,109, filed on Dec. 17, 2012, now abandoned.

(51) Int. Cl.
| | |
|---|---|
| *A61F 2/16* | (2006.01) |
| *G01M 11/08* | (2006.01) |
| *G01N 21/84* | (2006.01) |
| *G01N 21/64* | (2006.01) |

(52) U.S. Cl.
CPC .......... *A61F 2/1675* (2013.01); *A61F 2/1678* (2013.01); *G01M 11/081* (2013.01); *G01N 21/64* (2013.01); *G01N 21/8422* (2013.01); *A61F 2/167* (2013.01); *A61F 2/1662* (2013.01); *G01N 2021/8427* (2013.01)

(58) Field of Classification Search
CPC .... A61F 2/1675; A61F 2/1678; G01M 11/081
USPC ....................................................... 73/150 R
See application file for complete search history.

(56) References Cited

U.S. PATENT DOCUMENTS

| | | | |
|---|---|---|---|
| 5,772,861 A * | 6/1998 | Meredith, Jr. | ........ C23C 14/545 118/665 |
| 5,807,605 A | 9/1998 | Tingey et al. | |
| 6,252,237 B1 | 6/2001 | Ramthun et al. | |
| 6,283,975 B1 | 9/2001 | Glick et al. | |
| 6,962,670 B1 | 11/2005 | Hanson et al. | |
| 2003/0018353 A1 * | 1/2003 | Yang | ................. A61M 25/0045 606/194 |

(Continued)

FOREIGN PATENT DOCUMENTS

DE  10217950 A1  11/2002

OTHER PUBLICATIONS

International Search Report and Written Opinion for Application No. PCT/US2013/075822, dated Apr. 10, 2014, 10 pages.

*Primary Examiner* — Nimeshkumar D Patel
*Assistant Examiner* — Rodney T Frank
(74) *Attorney, Agent, or Firm* — Johnson & Johnson Surgical Vision, Inc.

(57) ABSTRACT

Methods for detecting a coating on a surface of an intraocular lens delivery device and methods of manufacturing the device are provided. A method includes forming the coating on the device, the coating including a lubricious-enhancing component and a fluorescing component, illuminating the fluorescing component to cause the fluorescing component to emit a glow, and determining characteristics of the coating on the device based on the glow of the fluorescing component.

20 Claims, 7 Drawing Sheets

(56) References Cited

U.S. PATENT DOCUMENTS

| | | | |
|---|---|---|---|
| 2004/0267359 A1* | 12/2004 | Makker | A61F 2/1664 623/6.12 |
| 2005/0005685 A1* | 1/2005 | Weber | B07B 1/02 73/61.71 |
| 2005/0147735 A1 | 7/2005 | Lowery et al. | |
| 2006/0229635 A1 | 10/2006 | Hu et al. | |
| 2007/0005135 A1 | 1/2007 | Makker et al. | |
| 2007/0260201 A1 | 11/2007 | Prausnitz et al. | |
| 2008/0250848 A1* | 10/2008 | Karki | G01N 1/38 73/54.01 |

* cited by examiner

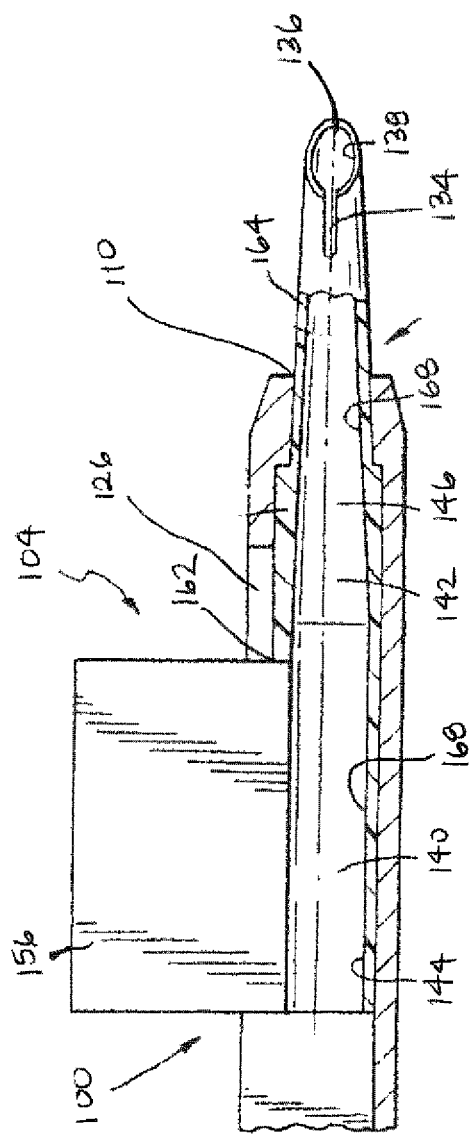
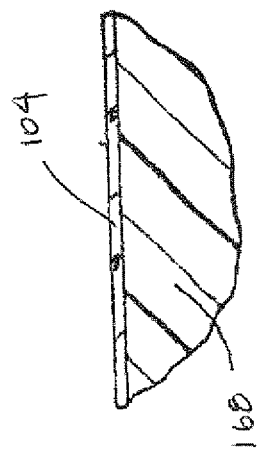
FIG. 4
FIG. 5

# DETECTING COATINGS ON INTRAOCULAR LENS INSERTION DEVICES AND METHODS OF MANUFACTURING THE DEVICES

This application is a divisional of and claims priority to U.S. application Ser. No. 13/717,109, filed on Dec. 17, 2012, the entire contents of which are hereby incorporated by reference in its entirety for all purposes as if fully set forth herein.

FIELD OF THE INVENTION

The present invention relates in general to insertion devices for delivering intraocular lenses into a patient's eye during vision correction surgery and, more particularly, to lens delivery cartridges and methods of manufacturing cartridges.

BACKGROUND OF THE INVENTION

Cataract surgery is commonly performed on an eye in which an originally clear, natural crystalline lens has become cloudy or opaque due to factors such as aging, prolonged exposure to radiation, or certain medical conditions. To provide vision correction to the affected eye, an artificial intraocular lens (IOL) is inserted adjacent or is used to replace the natural crystalline lens. Typically, IOLs are made up of an optically clear lens or "optic" that is secured in position within the eye via one or more flexible fixation members or "haptics". The haptics extend from the optic, and each haptic affixes directly to the eye.

Prior to surgery, the IOL is placed within an insertion device configured to deliver the IOL to the eye. In particular, the IOL is positioned within a load chamber of a cartridge of the insertion device. The load chamber defines a first lumen for receiving the IOL so that when the IOL is positioned therein, the cartridge may be manipulated to thereby roll, fold, or otherwise compress the IOL into a desired shape. An elongated inserter tube portion of the insertion device includes a second, tapered lumen adjacent and in communication with the first lumen for facilitating the passage of the folded IOL toward an exit of the insertion tube.

During surgery, a small incision of about 1-4 mm is made in the patient's eye. Preferably, the incision is as small as possible to reduce healing time. In some cases, a tool is inserted into the incision to emulsify the patient's natural lens. The emulsified material is then vacuum-suctioned from the eye. A tip of the insertion device is placed into the incision and the IOL is urged into the first lumen to be compressed or folded. As the IOL travels from the first lumen to the second lumen of the elongated inserter tube, the IOL is further compressed, rolled or otherwise manipulated into smaller dimensions suitable to pass through the 1-4 millimeter (mm) incision. The IOL then slips into the eye through the incision and automatically unfolds therein. In cases in which the natural lens remains in the eye, the folded or compressed IOL is placed adjacent the natural lens.

To ensure that the IOL is intact post-delivery, the inner surfaces of the cartridge and the elongated inserter tube are coated with a lubricity enhancing material to reduce an amount of force needed to pass the IOL through a small diameter of the insertion tube exit. Though damage to the IOL is rare when passed through the insertion tube exit, a mechanism to ensure lubricity of the cartridge's lumen and tip is adequate and uniform across the cartridge inner surface is desirable.

SUMMARY OF THE INVENTION

Methods for detecting a coating on a surface of a device are provided. A method includes forming the coating on the device, the coating including a lubricious-enhancing component and a fluorescing component, illuminating the fluorescing component to cause the fluorescing component to emit a glow, and determining characteristics of the coating on the device based on the glow of the fluorescing component.

In another embodiment, a method of manufacturing an IOL insertion device includes molding a cartridge of the insertion device, the cartridge having an inner surface defining a lumen for receiving an IOL, forming a coating on the inner surface of the cartridge, the coating including a lubricious-enhancing material and a fluorescing compound, energizing the fluorescing compound in the coating to cause a light emission, and measuring the light emission to determine a characteristic of the coating.

In another embodiment, an IOL device includes a molded cartridge having an inner surface defining a lumen, and a coating disposed on the inner surface of the molded cartridge comprising a lubricious material and a fluorescing compound.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which:

FIG. 4 is a longitudinal cross section view of the cartridge and inserter tube illustrated in FIG. 3, according to an embodiment.

FIG. 5 is a close up of the cross section view of an inner surface of the cartridge and inserter tube illustrated in FIG. 4, according to an embodiment.

DETAILED DESCRIPTION OF THE DRAWINGS

Figure 1:
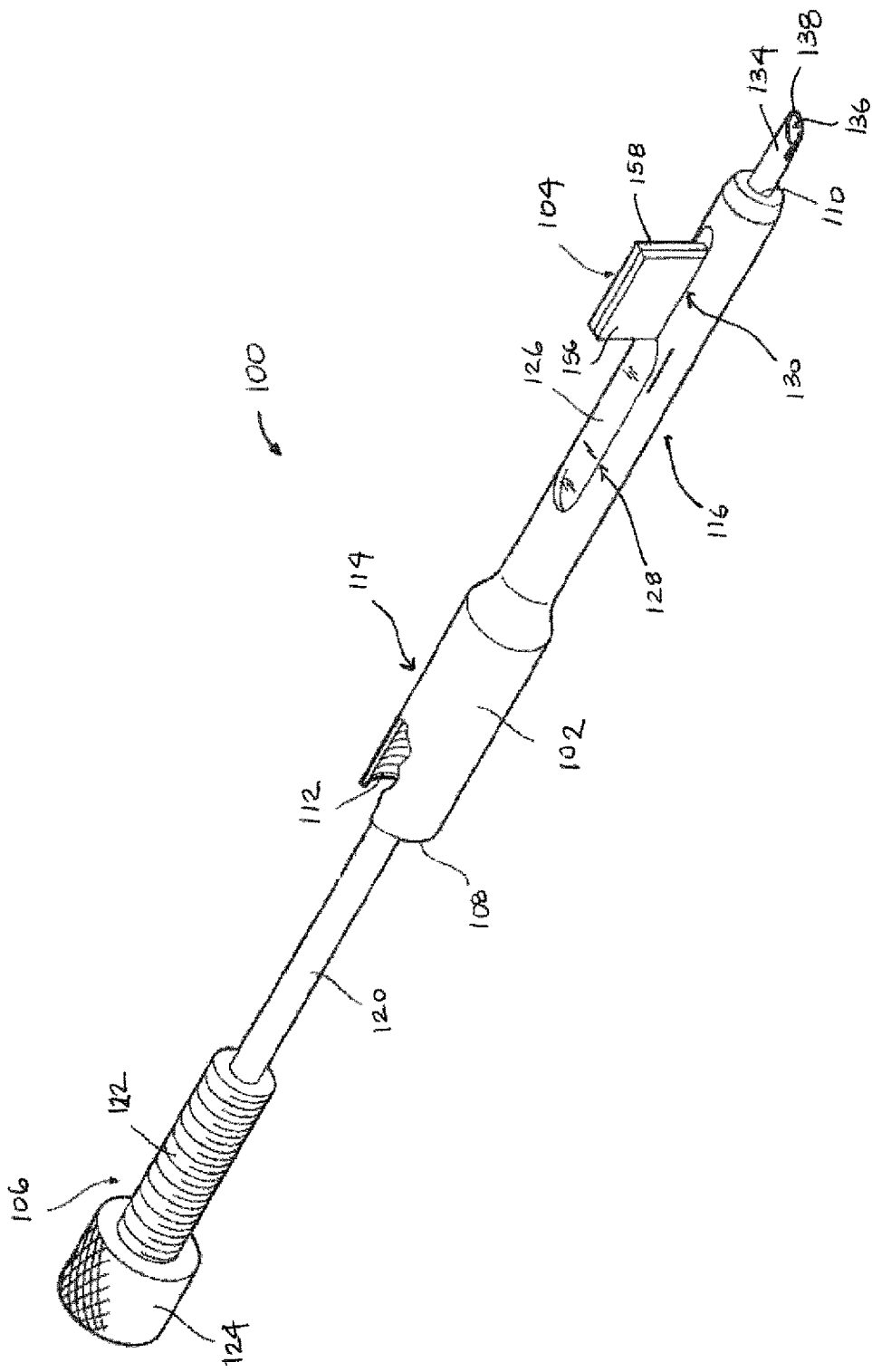
FIG. 1 is a perspective view of an intraocular lens (IOL) insertion device loaded onto a hand piece, according to an embodiment.
Figure 2:
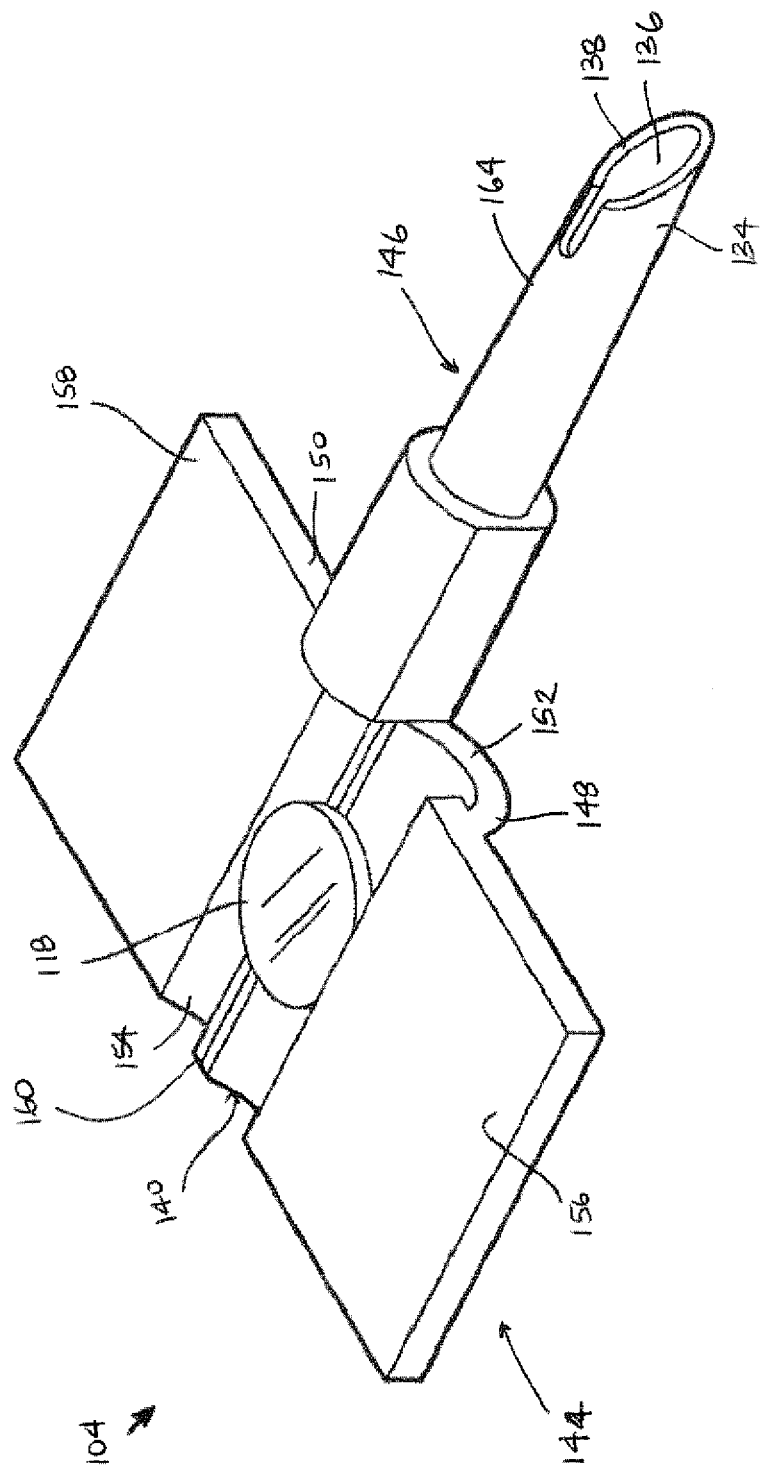
FIG. 2 is a perspective view of a cartridge in an open position and inserter tube for use with the IOL insertion device illustrated in FIG. 1, according to an embodiment.
Figure 3:
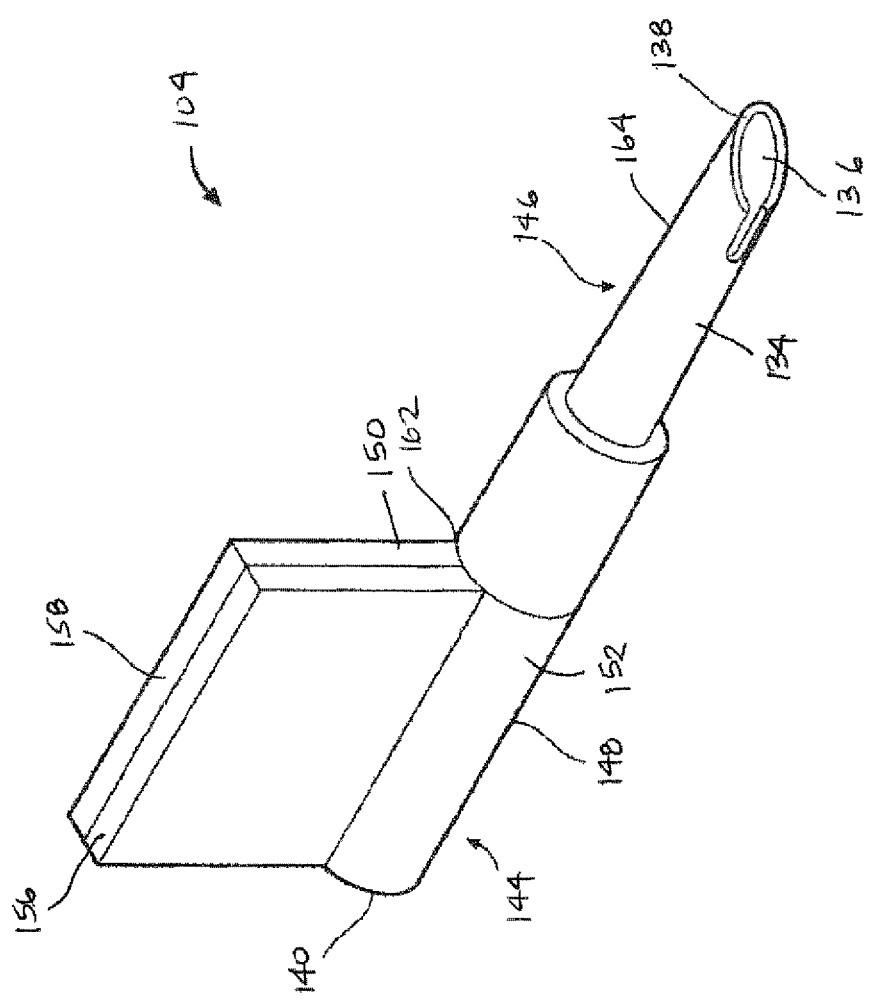
FIG. 3 is a perspective view of a cartridge in a closed position and inserter tube for use with the IOL insertion device illustrated in FIG. 1, according to an embodiment.

The following detailed description is merely exemplary in nature and is not intended to limit the inventive subject matter or the application and uses of the inventive subject matter. Certain terminology may also be used in the following description for the purpose of reference only, and thus` are not intended to be limiting. For example, terms such as "distal," "proximal," "inner," "outer," and "top" may refer to direction in the drawings to which reference is made and/or the orientation or location of portions of the components within a consistent but arbitrary frame of reference which is made clear by reference to the text and the associated drawings describing the component under discussion. Such terminology may include the words specifically mentioned above, derivatives thereof, and words of similar import.

Generally, the inventive subject matter is directed to intraocular lens (IOL) insertion devices, in particular, cartridges, and methods of manufacturing such devices. In an embodiment, the method includes coating an inner surface of the insertion device, where the inner surface defines a lumen for receiving an IOL. The coating includes a lubricity-enhancing material and a fluorescent compound. The lubricity-enhancing material minimizes friction between the IOL and the inner surface as the IOL passes through the lumen. The fluorescent compound is used in subsequent steps to allow easy inspection of the quality of the coating. The coating is applied by spray, brush, dip or other methods. The fluorescent compound is energized to thereby emit light, and the light emission is inspected. For example, the light emission is measured, and a determination is made as to whether a thickness or uniformity of the coating on the surface of the device is acceptable, based on the measurement of the light emission. If the thickness or uniformity is not acceptable, additional coating material is applied to the device to form a thicker and/or more uniform coating on the surface of the device.

With reference to FIGS. 1-4, various views of an intraocular lens (IOL) insertion device 100 and its components are provided. Insertion device 100 is generally elongated and configured similar to a syringe. In an embodiment, insertion device 100 includes a main body 102, a cartridge 104, and a plunger 106. Main body 102 is cylindrical and has openings 108, 110 at distal and proximal ends, and a longitudinal cavity 112 extending therebetween. Cavity 112 includes a plunger retention portion 114 and a narrower cartridge receiving portion 116. Plunger retention portion 114 is suitable in length for receiving at least a portion of plunger 106 and to allow plunger 106 to travel therethrough. Plunger 106, which is used to apply pressure on the IOL to thereby push the IOL 118 (FIG. 3) through an end of cartridge 104 and out device 100, includes a rod 120 suitably sized and shaped for moving through cavity 112 and into cartridge 104 to contact IOL 118, a retention body 122, and a handle 124 for a user to manipulate plunger 106. Retention body 122 is configured to be slid into plunger retention portion 114 and has a diameter larger than that of cartridge receiving portion 116. In an embodiment, one or both of the surfaces of retention body 122 and/or plunger retention portion 114 includes friction-enhancing components, such as a tacky substance or roughened surfaces, to provide added control for the user when the user applies pressure to handle 124. Distal opening 108, providing access into plunger retention portion 114, is larger in diameter than rod 120, but smaller in diameter than handle 124 to allow handle 124 to remain outside of cavity 112 during operation of insertion device 100.

Main body 102 optionally includes a longitudinal opening 126 formed along a portion of a length of cartridge receiving portion 116. Opening 126 provides access to cavity 112 and is dimensioned to accommodate the size and shape of cartridge 104. In an example, longitudinal opening 126 has a distal portion 128 having a length and width that corresponds to a length and width of cartridge 104 so that cartridge 104 can be selectively inserted into and/or removed from main body 102 via opening 126. A proximal portion 130 of opening 126 extending from distal portion 128 is narrower in length and width than distal portion 128 so that, as explained below, tabs 156, 158 of cartridge 104 can slide into and out of proximal portion 130 to thereby maintain cartridge 104 in a closed configuration during IOL delivery. Proximal opening 110 is configured such that an insertion tip 134 of cartridge 104 extends a desired length therethrough. Alternatively, proximal opening 110 aligns with an opening 136 at an end 138 of cartridge 104 to allow delivery of IOL 118 to a desired location.

As noted briefly above, cartridge 104 is configured to retain IOL 118. In this regard, cartridge 104 is generally tubular to define a first lumen or load chamber 140 and a second lumen or delivery channel 142 for IOL 118 to traverse during an insertion process. Cartridge 104 has a loading portion 144 capable of being rotated between an open configuration (see, e.g., FIG. 2) for loading and a closed configuration (see, e.g., FIG. 3) for loading IOL 118 into load chamber 140. An insertion portion 146 extends longitudinally from loading portion 144 to receive loaded IOL 118 when it travels from load chamber 140 to delivery channel 142.

Loading portion 144 has two complimentary pieces 148, 150 each including a grooved section 152, 154 and a tab section 156, 158. Grooved sections 152, 154 are connected to each other along adjacent longitudinal edges of grooved sections 152, 154. In an embodiment, the connection forms a hinge 160, which allows one of pieces 148 or 150 to be placed over the top of the other one of pieces 148 or 150. Hinge 160 is integrally formed as a semi-opaque seam between pieces 148, 150 or, alternatively, is a separate piece mounted between and connecting pieces 148, 150.

To form load chamber 140 when pieces 148, 150 are folded at hinge 160, grooved sections 152, 154 each includes substantially similarly configured semicircular longitudinal channels, each channel forming one half of load chamber 140. A width of the two semicircular channels is preferably is greater than a diameter of IOL 118 so that when IOL 118 is positioned across the semicircular channels, IOL 118 folds over itself as pieces 148, 150 are manipulated into the closed configuration. Tab sections 156, 158 extend from grooved sections 152, 154 away from hinge 160 and are provided as gripping surfaces to allow a user to easily manipulate pieces 148, 150 between the open and closed configurations. Although depicted as substantially rectangular, in other embodiments, tab sections 156, 158 are each semicircular, square, semiovular, or another shape suitable for forming tabs that are sufficiently large such that the user avoids contacting interior surfaces of grooved sections 152, 154. Additionally, although tab sections 156, 154 are shown as substantially equal in size, one is larger than the other in alternate embodiments.

As noted previously, cartridge 104 includes insertion portion 146, which receives IOL 118 from load chamber 140 during the delivery process. Insertion portion 146 is connected to and extends from an edge defining an end of grooved sections 152, 154. To prevent contamination and damage to IOL 118 during delivery, insertion portion 146 is configured such that an opening into delivery channel 142 aligns with and is substantially the same size as an opening into load chamber 140. In an embodiment, inner surfaces of load chamber 140 and delivery channel 142 are substantially smooth to avoid inadvertently trapping IOL 118 within either space. Outer surfaces of each of loading and insertion portions 144, 146 are substantially smooth, except a seam 162 can be included at a location at which the two meet.

A proximal end of insertion portion 146 includes a tapered tube 164 having a portion of delivery channel 142 formed therethrough. According to an embodiment, delivery channel 142 is also tapered and has an increasingly smaller diameter such that proximal opening 136 on insertion tip 134 has a diameter suitable for delivering IOL 118 into a patient's eye through an incision having a length in a range of about 1 millimeters (mm) to about 5 mm, and more preferably in a range of less than about 2 mm. In this regard, insertion tip 134 preferably has a diameter that is less than the aforementioned ranges.

To ensure smooth delivery of IOL 118 and to reduce a likelihood of damage thereto, cartridge 104 is formed from materials capable of withstanding high frictional forces during the IOL 118 delivery process. Suitable materials for cartridge 104 include, but are not limited to, materials having a characteristic toughness that allows >150% elongation or strain without damaging the polymer (e.g., cracking or ripping), for example between about 150% and about 500%, or between about 250% and 600%. Further, the polymeric materials have tensile strengths preferably >1000 psi, such as between about 1000 psi and about 10,000 psi, or about 5000 psi and 8000 psi.

Cartridge 104 is formed from hydrophilic or hydrophobic polymers with a hardness greater than about 50 D, preferably between about 50 D and about 85 D. In an embodiment, cartridge 104 is formed from an aromatic polyurethane with a hardness of between about 55 D and about 75 D, for example the Pellethane, Tecothane, Texin, and Esthane families of aromatic polyurethane. Alternatively, cartridge 104 is formed from aliphatic polyurethane with a hardness between about 60 D and about 72 D, for example Tecoflex. It is also noted that the "D" numbers provided above are measures of hardness. Specifically, the numbers provided above indicate the Shore (Durometer) hardness of the material, which is basically a measure of the material's resistance to indentation. The numbers do not directly measure the material's toughness. However, polymeric materials are commonly identified by their Shore hardness, and the materials identified above have favorable toughness. Material exhibiting one or more of the aforementioned properties include, but are not limited to polyurethane polymers; polyethylene, polypropylene, styrene related copolymers, such as but not limited to, acrylic butyldiene styrene (ABS), styrene butyldiene styrene (SBS), and/or high impact polystyrene (HIPS); polyester polymers; and polymeric blends or copolymers thereof.

Polyurethane polymers may have a number of different compositions. For instance, particular polyurethanes may be aromatic or aliphatic and may be hydrophilic or hydrophobic. Such polyurethanes may have different mechanical properties, such as but not limited to toughness characteristics, other physical properties, and other surface properties. Further regarding physical properties of polymeric materials described herein whether they be solids, gels, fluids, liquids or the like, hydrophobic polymeric materials generally have toughness characteristics and hydrophilic polymeric materials generally have lubricious characteristics. These characteristics are by no means limiting, but exemplary.

To reduce the likelihood of damage to IOL 118 during delivery and to ensure lubricity of delivery channel 142, selected portions of cartridge 104 include a coating 168, as illustrated in FIG. 5. For example, a coating 168 is disposed on inner surfaces of cartridge 104, such as on surfaces defining delivery channel 142, and on insertion tip 134.

Coating 168 is formed from materials including a lubricious-enhancing component and a fluorescing component or fluorescing compound. The lubricious-enhancing component includes materials having characteristics, including but not limited to one or more hydrophilic polymeric material, such as hydrophilic polyurethane, polyvinylpyrrolidone, polyacrylic acid, polyacrylamides, polyhydroxyethyl methacrylate, polyethylene oxide, polyethylene glycol and/or hyaluronan, or the like.

The hydrophilic polymeric material contains reactive groups or substituents that allow at least limited covalent attachment to cartridge 104, in an embodiment. For example, the hydrophilic material may be applied to cartridge 104 as a precursor material and hence, includes substituent groups effective to enhance the stability, for example the storage stability or shelf life, of cartridge 104 relative to an identical cartridge including a lubricity enhancing component without the substituent groups. Preferably, the substituent groups are effective to reduce hydrolysis of the lubricity enhancing coating relative to an identical lubricity enhancing coating or component without the substituent groups. In an embodiment, the substituent groups are not —OH groups, that is, are non-hydroxy groups. For instance, the substituent component may be selected from the class consisting of hydrocarbyl groups, substituted hydrocarbyl groups, and mixtures thereof, preferably such groups having 1 to about 4 carbon atoms per group. In another embodiment, the substituent component is selected from alkoxy groups, preferably alkoxy groups having 1 to about 4 carbon atoms per group, and mixtures thereof. In still another embodiment, the substituent component includes one or more methoxy groups.

According to an embodiment, the lubricity-enhancing component is derived from a hydrophilic, water soluble precursor component or material including the aforementioned substituent component or groups, an alkylene oxide component and the reactive substituent component or groups effective to covalently bond with the substrate (i.e., the polymeric material of cartridge 104). Such reactive groups, or at least a portion of such reactive groups, are effective to form homopolymers of the precursor material. The alkylene oxide component, for example, in the form of a polyalkylene glycol component and the like, may be selected from, for example, ethylene oxide components, propylene oxide components, and the like, and mixtures thereof. The alkylene oxide component is preferably an ethylene oxide component, for example a polyethylene glycol component. The reactive substituent component or groups are preferably selected from ethylenically unsaturated groups, and are more preferably selected from vinyl groups, acrylic groups, methacrylic groups, and the like, and mixtures thereof. In an embodiment, the precursor material of the lubricity enhancing component is a hydrophilic, water soluble acrylic-based monomer such as methoxy polyethylene glycol monomethacrylate (mPEGMA) of similar or differing molecular weights. In an another embodiment, the precursor material of the lubricity enhancing component is a hydrophilic, water soluble urethane-based polymer such as ether linkage and ester linkage polyurethane.

The fluorescing component is a material that is capable of emitting a glow and that does not adversely affect the stability of coating 168. Suitable materials for use as the fluorescing compound include, but are not limited to, biocompatible fluorescing compounds such as fluorescein, sodium salts and/or derivatives of fluorescein, and the like.

Coating 168 also includes a crosslinking agent, such as polyfunctional aziridine, polyfunctional carbodiimide, isocyanate, and the like.

Figure 6:
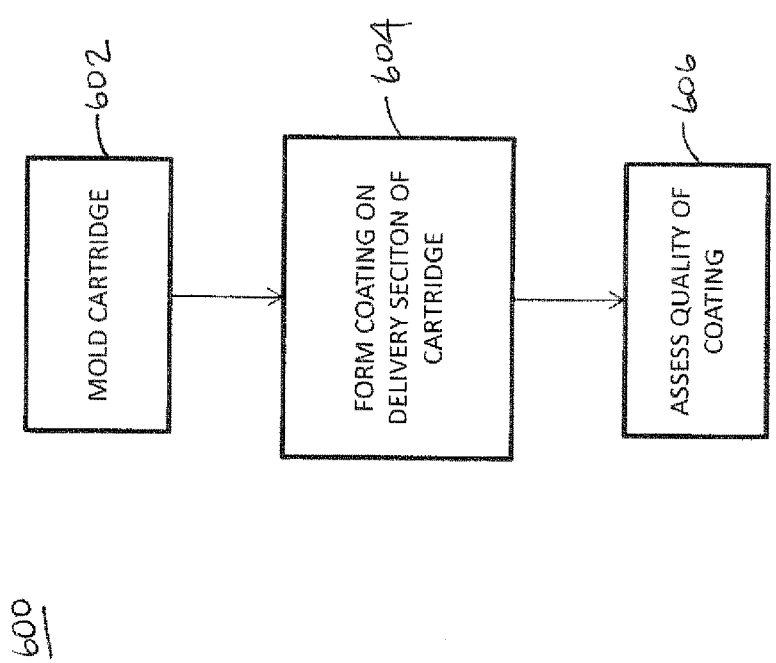
FIG. 6 is a flow diagram of a method of manufacturing an IOL insertion device, according to an embodiment.

FIG. 6 is a flow diagram of a method 600 of forming cartridge 104. In an embodiment, cartridge 104 is molded using a suitably configured mold at 602. Cartridge 104 is molded as a single piece of material and/or is made from a blend of two or more different ones of the above mentioned materials. Alternatively, different portions of cartridge 104, for example, loading portion 144 and insertion portion 146 are formed as separate components from one or more materials and are welded, adhered, coupled, or otherwise joined together. Alternatively, cartridge 104 is comolded from two or more materials that are extruded and/or injection molded to form a single piece to thereby yield a component having different physical properties at different locations thereon.

A coating 168 is formed in insertion portion 146 of cartridge 104 at 604. In particular, coating 168 is formed over an inner surface of cartridge 104 defining delivery channel 142 and over a surface of insertion tip 134. In an embodiment, insertion portion 146 is formed from lubricious-enhancing and fluorescing material and co-molded with the remainder of cartridge 104. In another embodiment, the fluorescing material and one or more of the lubricious materials described above is used to form a lubricious coating over the selected surfaces of cartridge 104 by brushing, spraying or otherwise applying a thin layer of the materials on the selected surfaces of cartridge 104. For example, a dispersion is formed from the fluorescing material, the lubricious-enhancing material, and a cross-linking agent. In an embodiment, a suitable amount of fluorescing compound, such as an amount suitable for forming between about 0.1% to about 5% dry concentration of fluorescing material in dry dispersion, is dissolved in water to form solution. Substantially equal amounts of the lubricious-enhancing component and a crosslinking agent are added to the fluorescing compound solution to form the dispersion including the about 0.1% to about 5% dry concentration of fluorescing material.

Optionally, prior to receiving the dispersion, the inner surfaces of cartridge 104, in particular, those surfaces on which coating 168 is to be applied, are treated with plasma to enhance adhesion of coating 168 thereto. In an embodiment, cartridge 104 is exposed to plasma for a suitable duration to prime surfaces of delivery channel 142. The plasma is derived from one or more gases, including but not limited to oxygen, helium, nitrogen, argon, nitrous oxide, carbon dioxide and the like, and is delivered via a PS-150 plasma unit or another suitable plasma delivery device. The plasma includes oxygen at a flow rate of 20 cc/min and argon at a flow rate of 10 cc/min. The duration of treatment is about 5 minutes.

The dispersion is applied to cartridge 104 via brush application, spray application, injecting the solution into delivery channel 142, dipping cartridge 104 into the solution including the fluorescing compound, or any other suitable application method.

According to an embodiment in which the dispersion is applied to cartridge 104 as a precursor material, cartridge 104, and more specifically, insertion portion 146 of cartridge 104, is prepared for receiving the precursor material. After plasma treatment, the dispersion is applied to a wall of cartridge 104, for instance by spraying, brushing, immersion, irrigation, or the like. The coated, or wetted, wall is then exposed to conditions effective to cause the precursor material in the dispersion to form a lubricity enhancing component, or coating, having covalent bonds with the polymeric material of the tube. Subsequently, the wetted wall is post-cured at conditions effective to form coating 168 and to enhance the stability thereof.

In an embodiment, the precursor material includes radical initiators, for instance UV and/or thermal radical initiators. The step of causing the precursor material to form a covalently bonded lubricity enhancing component preferably includes exposing the wetted wall to conditions suitable for activating the initiator or initiators. In an embodiment in which the precursor material includes both UV and thermal radical initiators, the step of exposing the wetted wall to conditions suitable for activating the initiator or initiators includes a first stage of exposing the wetted wall to ultraviolet light to form a covalently bonded coating 168 on the interior wall, and a second stage of exposing the covalently bonded coating 168 on the wall to elevated temperatures for a time sufficient to enhance the stability of the covalently bonded coating 168. After coating 168 has been exposed to the UV light and/or elevated temperatures, unreacted monomers are removed from cartridge 104 surface, for instance by washing. Any suitable UV initiator and/or thermal initiator may be employed provided such materials have no substantial detrimental effect on the inserter, on the IOL to be inserted or on the patient in whose eye the IOL is inserted.

Next, the quality of coating 168 is assessed at 606. Energy is provided to the fluorescing compound to cause the fluorescing compound to emit a glow. Ultraviolet (UV) light is directed at cartridge 104 to energize the fluorescing compound. For example, a UV lamp or other device capable of emitting light within a UV wavelength range (e.g., 100 nanometers (nm) to 600 nm) is powered on and when the UV light interacts with the fluorescing compound, electrons in the fluorescing compound excite causing the compound to emit light or a glow. Measurements of the resulting glow intensity are obtained using a light measuring device, such as a handheld photodetector, a lux meter or other type of light meter configured to detect the intensity of the light emitted across a surface of cartridge 104 (including surfaces of coating 168).

The intensity of the glow can be affected by factors such as the concentration of the fluorescing compound present in coating 168, the intensity of the UV light used to excite the fluorescing compound, the thickness of coating 168 within which the fluorescing compound is disposed, and/or the uniformity of coating 168. Hence, such factors can be used to determine the characteristics of coating 168. In an example, a particular concentration of the fluorescing compound for inclusion in coating 168 is selected, coating 168 is formed, and UV light of a desired intensity is directed at coating 168. The intensity of the emitted glow is measured and compared to reference values. For instance, using measurements taken from a reference location on coating 168 as reference values, light intensity measurements obtained from other locations on coating 168 are compared to the reference values to determine thickness of coating 168. In particular, those light intensity measurement values greater than the reference values indicate areas of coating 168 having a greater thickness than the reference location, while light intensity measurement values that are less than the reference values indicate areas of coating 168 that are thinner than the reference location. Alternatively or additionally, the thickness of coating 168 can be determined by comparing the measurements of the light emitted by the excited fluorescing compound in coating 168 to a visible light of yellow index. To measure the color of the light emitted, a spectrophotometer, such as an Ultrascan PRO™ provided by Hunter Associates Laboratory, Inc. of Reston, Va., or another instrument capable of measuring visible color is used. A higher yellow index value indicates a greater thickness of coating 168. To determine the uniformity of coating 168, light intensity measurements across substantially an entirety of coating 168 are obtained and a determination is made as to whether the measurements fall within a particular range.

If the values obtained above indicate either a uniformity or thickness of coating 168 that is less than desirable, coating 168 is deemed unacceptable. Accordingly, cartridge 104 is returned to manufacturing to be re-coated at 604. If the values indicating the uniformity or thickness of coating 168 are equal to or exceed the corresponding reference values, the coating 168 is deemed acceptable and method 600 ends.

The following examples are presented to illustrate aspects and features of various embodiments of the present inventive subject matter, and are not to be taken as limiting the inventive subject matter in any respect.

Example 1

Cartridges formed from polypropylene were obtained and surfaces thereof, in particular, inner surfaces forming delivery channels, were treated with plasma. The cartridges then were coated with dispersions of fluorescein.

Specifically, cartridges were each coated with dispersions including concentrations of about 5.0%, 1.0%, and 0.5% dry weight of fluorescein. To form a dispersion including a concentration of about 5.0% dry weight of fluorescein, about 0.490 gram (g) of fluorescein sodium salt was weighed and placed in a 100 milliliter (mL) propylene bottle, and about 50.02 g of polyurethane dispersion (solid content about 20%) and about 0.50 g of polyfunctional aziridine was added to the same bottle and capped. For a concentration of about 1.0% dry weight of fluorescein, about 0.1083 g of a sodium salt of fluorescein was weighed and placed in a 100 mL polypropylene bottle, and an amount of polyurethane dispersion (solid content about 20%) weighing about 51.94 g and about 0.50 g of polyfunctional aziridine were placed in the same bottle and capped. For a dispersion including a concentration of about 0.5% dry weight of fluorescein, about 0.049 g of a sodium salt of fluorescein was weighed and placed in a 100 mL polypropylene bottle, and an amount of polyurethane dispersion (solid content about 20%) weighing about 51.65 g and about 0.50 g of polyfunctional aziridine were placed in the same bottle and capped. Each bottle was placed on a stir plate and each dispersion was mixed for about 15 minutes using a stir bar. The dispersions were delivered into the delivery channels of corresponding cartridges via a plastic pipette until a meniscus formed in the delivery channel. The dispersions were allowed to run out of the cartridges via gravity. The cartridges were placed in a centrifuge to spin-off remnants of the dispersions and subsequently placed on a hot plate at about 60° Celsius (C) for about 10 minutes to dry.

Other cartridges were coated with dispersions including concentrations of 0.1% and 0.05% dry weight of fluorescein. The dispersion including the concentration of 0.1% dry weight of fluorescein was formed by weighing a sodium salt of fluorescein in an amount of about 0.1070 g and placing the fluorescein sodium salt into a tube containing 10 mL of pure water. The tube was shaken until all of the fluorescein sodium salt dissolved into the water. An amount of a polyurethane dispersion (solid content about 20%) weighing about 51.34 g and about 0.50 g of polyfunctional aziridine were placed in a 100 mL polypropylene bottle. About 1 mL of the fluorescein sodium salt solution was added to the bottle, and the bottle was capped. The dispersion including the concentration of 0.05% dry weight of fluorescein was formed by weighing a sodium salt of fluorescein in an amount of about 0.018 g and placing the fluorescein sodium salt into a tube containing about 10 g of pure water. The tube was shaken until all of the fluorescein sodium salt dissolved into the water. An amount of a polyurethane dispersion (solid content about 20%) weighing about 49.87 g and about 0.50 g of polyfunctional aziridine were placed in a 100 mL polypropylene bottle. About 2.73 g of the fluorescein sodium salt solution was added to the bottle, and the bottle was capped.

Each bottle was placed on a Vortex mixer and shaken. A plastic pipette was used to deliver the dispersions into the delivery channels of corresponding cartridges until a meniscus formed in the delivery channels. The dispersions were allowed to run out of the cartridge via gravity. A vacuum was used to remove any dispersion remaining on the cartridge, and the cartridges were then placed in a vacuum oven at about 60° Celsius (C) for about 10 minutes to dry.

Example 2

Each cartridge was explored using an ultraviolet lamp at 254 nanometer (nm) and 365 nm wavelengths. As shown in Table 1, fluorescein was detected on all of the cartridges except those coated with 0.05% dry weight concentration of the fluorescein dispersion. Non-coated portions of the cartridges did not fluoresce.

TABLE 1

| % dry concentration of fluorescein in dry dispersion | 5 | 1 | 0.5 | 0.1 | 0.05 |
|---|---|---|---|---|---|
| Fluorescein detected by UV 254 nm & 365 nm | shine | shine | shine | shine | no shine |

Example 3

The coated cartridges including concentrations of about 5.0%, 1.0%, 0.5%, and 0.1% dry weight of fluorescein of Example 1 and uncoated cartridges were placed in a tray and a UV lamp emitting UV light at a wavelength of 325 nm was directed at the tray. The coated cartridges emitted a glow, while the uncoated cartridges did not. Cartridges coated with the higher concentration of dispersion (e.g., 1% dry weight concentration) emitted a brighter light than those coated with the lower concentration of dispersion. Additionally, those portions of the coated cartridges having thicker coatings, for example, the tips of the coated cartridges, appeared to be brighter than those portions having thinner coatings. Since coating uniformity is required, the cartridges having thicker portions were rejected.

Example 4

Figure 7:
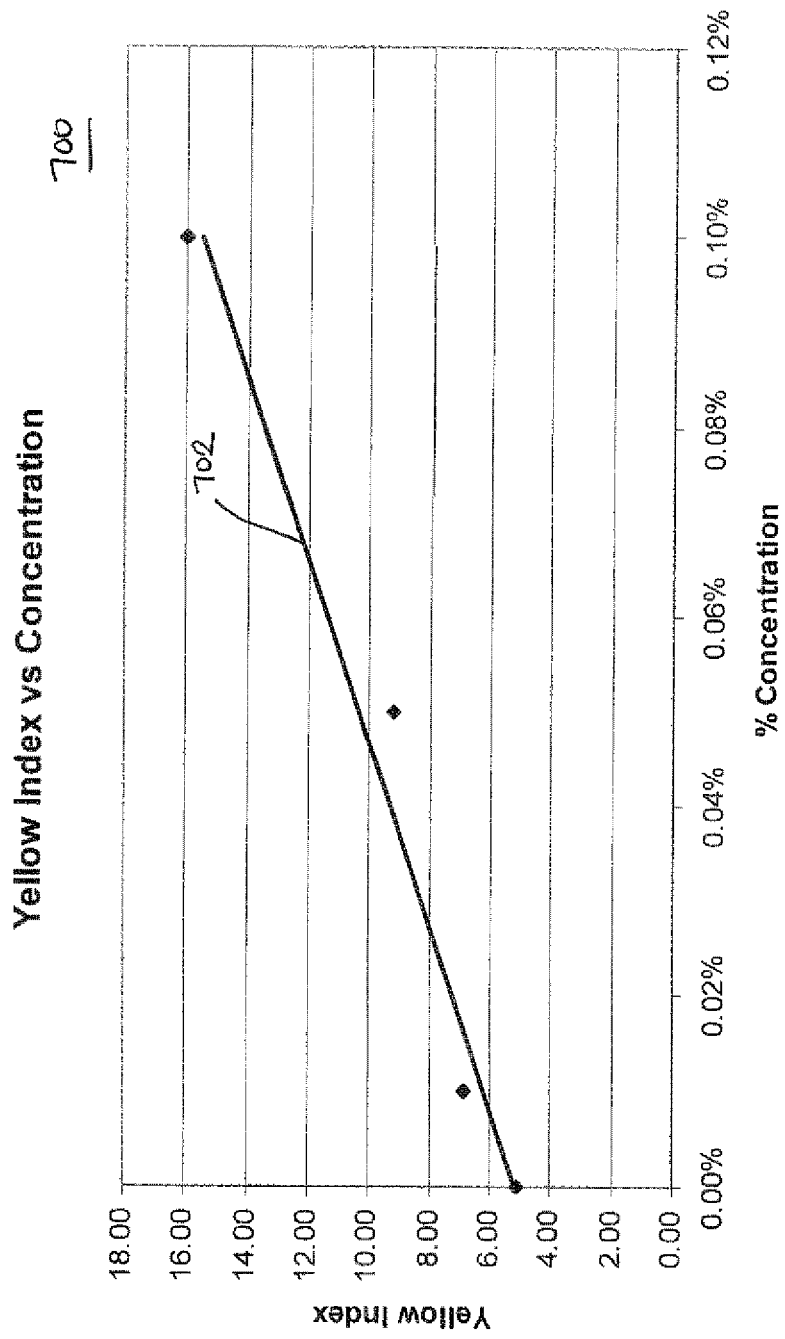
FIG. 7 is a graph showing an increase in yellow index value as a concentration of fluorescing compound increases.

The yellow index was measured for cartridges including concentrations of about 1.0%, 0.5%, and 0.1% dry weight of fluorescein. The yellow index values were measured by employing an UltraScan PRO chromameter sold by Hunter Associate Laboratory of Reston, Va. FIG. 7 is a graph 700 plotting the measured results. In particular, graph 700 includes a y-axis including yellow index values in a range of from 0.00 to 18.00 and an x-axis including dry weight concentration of the measured cartridge. Plot line 702 shows the yellow index value increases as the dry weight concentration of the fluorescein in the coating of the cartridge increases.

Example 5

To determine whether thickness of coating 168 could be detected, the yellow index for different coating thicknesses were measured. Three 43 mm aluminum pans were used and solutions of about 2.01 g, about 1.10 g, and about 0.22 g of the 0.1% dry weight concentration of the fluorescein sodium salt dispersion were poured into respective pans. Each pan was dried at room temperature overnight and then placed in an oven at 110° C. for one hour. The pans were cooled to room temperature and each resulting film was peeled from the pans. The thickness of each film was measured using a micrometer device and the yellow index of each was measured using the UltraScan PRO chromameter. Another set of three films was prepared in a similar manner as described previously, except a 0.5% dry weight concentration of the fluorescein sodium salt dispersion was used. Lastly, a third set of three films was also prepared in a similar manner as described previously, except a 1% dry weight concentration of the fluorescein sodium salt dispersion was used.

Figure 8:
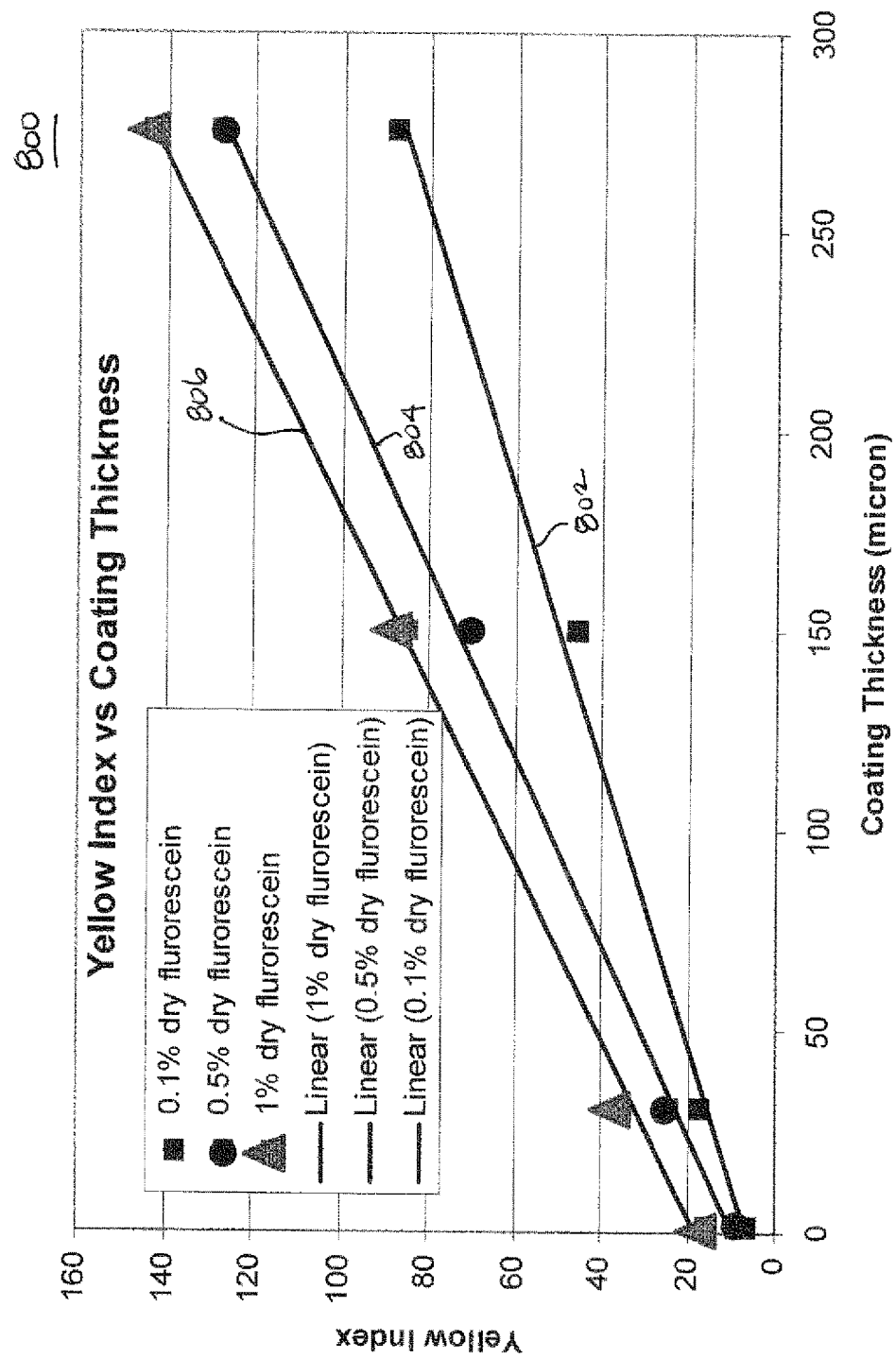
FIG. 8 is a graph showing an increase in yellow index value as a thickness of a coating including fluorescing compound therein increases.

FIG. 8 is a graph 800 showing the resulting measurements obtained from the testing conducted above and from measurements taken from cartridges including concentrations of about 1.0%, 0.5%, and 0.1% dry weight of fluorescein formed in Example 1. Plot lines 802, 804, and 806 each initiate on the left at plots of the measurements taken from cartridges including concentrations of about 1.0%, 0.5%, and 0.1% dry weight of fluorescein formed in Example 1. The remaining measurements from the testing described above are plotted to the right of the aforementioned plots. Each of the plot lines 802, 804 and 806 generally shows that as thickness of the coating increases, the yellow index measurement increases as well. Additionally, the yellow index measurements are greater for films having higher concentrations of fluorescein sodium salt.

By using relatively small amounts (e.g., about 0.1% to about 5.0% dry weight concentration) of fluorescein, or another biocompatible fluorescing compound, the quality of lubricious coatings on cartridges can be easily, quickly, and safely ascertained. The fluorescein remains on the cartridge during lens delivery, thus minimizing potential irritation experienced by a patient's eye.

While at least one exemplary embodiment has been presented in the foregoing detailed description of the inventive subject matter, it should be appreciated that a vast number of variations exist. It should also be appreciated that the exemplary embodiment or exemplary embodiments are only examples, and are not intended to limit the scope, applicability, or configuration of the inventive subject matter in any way. Rather, the foregoing detailed description will provide those skilled in the art with a convenient road map for implementing an exemplary embodiment of the inventive subject matter. It being understood that various changes may be made in the function and arrangement of elements described in an exemplary embodiment without departing from the scope of the inventive subject matter as set forth in the appended claims.

What is claimed is:

1. A method of detecting a characteristic of a coating on an inner surface of an intraocular lens (IOL) cartridge defining a lumen for receiving an IOL comprising:

forming the coating on the inner surface of the IOL cartridge, the coating including a lubricious-enhancing component, a fluorescing component;

illuminating the fluorescing component to cause the fluorescing component to emit light; and determining characteristics of the coating on the inner surface of the IOL cartridge based on a light intensity of the fluorescing component, including measuring a first light intensity at a first reference location on the coating and setting the first light intensity as a reference value, comparing light intensity measurements taken from other locations on the coating to the reference value and determining a uniformity of the thickness of the coating over the inner surface of the IOL cartridge based on the comparisons.

2. The method of claim 1, wherein the lubricious-enhancing component comprises a hydrophilic polymeric material.

3. The method of claim 1, wherein the fluorescing component comprises fluorescein.

4. The method of claim 1, wherein forming the coating includes forming a dispersion including a concentration of about 0.01% to about 5.0% of the fluorescing component in the coating and applying the dispersion to the inner surface of the IOL cartridge.

5. The method of claim 4, wherein forming the coating further comprises mixing the fluorescing component with the lubricious-enhancing component and a crosslinking agent to form the dispersion.

6. The method of claim 1, wherein the crosslinking agent is selected from the group consisting of polyfunctional aziridine, polyfunctional carbodiimide, and isocyanate.

7. The method of claim 1, further comprising exposing the inner surface of the IOL cartridge to plasma to wet the inner surface, prior to forming the coating.

8. The method of claim 1, further comprising applying another layer of coating material to the coating, if the uniformity of the thickness of the coating falls outside an acceptable range.

9. The method of claim 1, further including comparing a color of the light intensity measurements taken with a yellow index table.

10. The method of claim 9, wherein comparing the color of the light intensity measurements taken with a yellow index table determines a thickness of the coating, the method further includes applying another layer of coating to the inner surface of the IOL cartridge if the thickness of the coating is determined to be insufficient.

11. The method of claim 1, wherein the step of measuring a first light intensity is done with a device selected from the group consisting of a hand-held photodetector and a lux meter.

12. A method of manufacturing an intraocular lens (IOL) insertion device comprising:

molding a cartridge of the insertion device, the cartridge having an inner surface defining a lumen for receiving the IOL;

forming a coating on the inner surface of the cartridge, the coating including a lubricious-enhancing material and a fluorescing component;

energizing the fluorescing compound in the coating to cause a light emission; and measuring the light emission to determine a characteristic of the coating, including comparing a color of the light emission with a yellow index table to determine a thickness of the coating.

13. The method of claim 12, further comprising applying another layer of coating to the inner surface of the cartridge, if the thickness of the coating is determined to be insufficient.

14. The method of claim 12, further comprising exposing the inner surface of the cartridge to plasma to wet the inner surface, prior to forming the coating.

15. The method of claim 14, wherein the lubricious-enhancing material includes thermal radical initiators and ultraviolet radical initiators, and forming the coating includes exposing the lubricious-enhancing material to ultraviolet light and to elevated temperatures for a time sufficient to enhance stability of a resultant covalently bonded coating formed on the inner surface of the cartridge.

16. The method of claim 12, wherein the measuring the light emission includes measuring a color of the light emission in multiple locations across the coating and comparing the color measured at the multiple locations to a yellow index to determine a thickness of the coating at the multiple locations.

17. The method of claim 12, wherein the fluorescing compound comprises fluorescein.

18. The method of claim 12, wherein the coating includes a crosslinking agent.

19. The method of claim 12, further comprising measuring a first light intensity at a first reference location on the coating and setting the first light intensity as a reference value, comparing light intensity measurements taken from other locations on the coating to the reference value, determining a uniformity of the thickness of the coating over the surface of the device based on the comparisons, and applying another layer of coating material to the coating if the uniformity of the thickness of the coating falls outside an acceptable range.

20. The method of claim 12, wherein the step of measuring the light emission is done with a spectrophotometer.

* * * * *